United States Patent

Burlatsky et al.

[11] Patent Number: 5,846,394
[45] Date of Patent: Dec. 8, 1998

[54] METHOD AND APPARATUS FOR CARRYING OUT ELECTROPHORESIS IN FRACTAL FIELDS

[75] Inventors: Sergei F. Burlatsky, Cambridge; Leo A. Smolensky, Concord, both of Mass.

[73] Assignee: LSR Technologies, Inc., Acton, Mass.

[21] Appl. No.: 862,317

[22] Filed: May 23, 1997

[51] Int. Cl.[6] .......................... G01N 27/26; G01N 27/447
[52] U.S. Cl. .......................... 204/458; 204/457; 204/608; 204/609
[58] Field of Search .................................. 204/457, 458, 204/608, 609

[56] References Cited

U.S. PATENT DOCUMENTS

5,084,157  1/1992  Clark et al. .............................. 204/609

Primary Examiner—Robert J. Warden
Assistant Examiner—John S. Starsiak, Jr.
Attorney, Agent, or Firm—Hill & Simpson

[57] ABSTRACT

A method and apparatus for carrying out electrophoretic separation is provided which imparts a fractal field component to the particles themselves or to the medium in which the particles are to be separated which, in combination with a steady field component, provides for a fast electrophoretic separation method that can be used on molecules and particles of a larger size than currently available electrophoretic methods.

26 Claims, 6 Drawing Sheets

METHOD AND APPARATUS FOR CARRYING OUT ELECTROPHORESIS IN FRACTAL FIELDS

BACKGROUND OF THE INVENTION

The present invention relates generally to techniques for separating larger particles or molecules from smaller particles or molecules. More particularly, the present invention is directed toward improved methods and apparatuses for carrying out electrophoresis whereby smaller particles or molecules that are suspended in a medium or matrix are separated from larger particles or molecules. Still more specifically, the present invention provides an apparatus and a method for generating a fractal field in a separation medium or matrix and carrying out separation by electrophoresis in the fractal field.

Electrophoresis is a useful method or process for the separation of large molecules suspended in a support matrix or medium. In electrophoresis, the molecules to be separated are charged and moved through the support medium under the influence of an electric field. Because larger molecules move through the medium at a slower rate than smaller molecules, the molecules may be separated by size. Electrophoresis is particularly important in the study of chromosomes, proteins and nucleic acids because it assists scientists in separating mixtures of these compounds by size, thereby enabling the scientist to study individual compounds.

In order for electrophoresis to successfully separate molecules by size, the mobility of the molecules must depend on their size. In the case of polymer chains, such as DNA, the chain mobility, $\mu_e$, must be dependent upon chain length, L. However, in a free solution, the effective chain mobility $\mu_e$ is not dependent upon the chain length L because both the effective driving force and the effective drag force are both directly proportional to chain length L and the chain mobility is proportional to the ratio of the effective drag force to the effective friction force. As a result, the direct proportional relationship between the effective driving force and the effective drag force on the chain length L is canceled from the ratio and the chain mobility in a free liquid solution, $\mu_f$, does not depend on L and there is no separation or a poor separation of longer chains from shorter chains.

Thus, the separation of long chain molecules by electrophoresis cannot be effectively conducted in a free liquid solution. Therefore, separation of long chains by electrophoresis is typically conducted in a gel medium. Agarose is a particularly suitable gel because it does not bind to the DNA molecules. Agarose also has a relatively large pore size which makes it particularly suitable for use with DNA and other long chain molecules.

The mobility of a polymer chain in a gel under a driving force imposed by electric field is less than that of a chain in a free liquid solution. This is true because, in a gel, the maximum driving force is achieved only when the chain is in alignment with the direction of the electric field. When the chain is perpendicular to the electric field, there is no component of the driving force that will drive the chain forward in the direction of the electric field. Specifically, it has been shown that the driving force is equal to $E|h_z|\rho$, where $h_z$ is the distance between the leading and trailing ends of the chain measured in the z direction, E is the electric field directed in the z direction and $\rho$ is the linear charge density.

Figure 2:
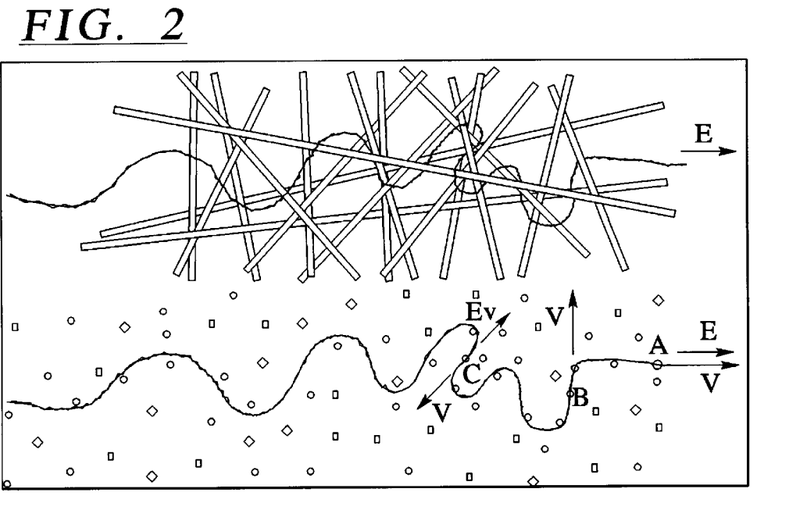
FIG. 2 illustrates a polymer chain disposed in a random array of gel fibers and a corresponding tube model of the polymer chain disposed in an array of obstacles.

An example of this phenomenon is illustrated in FIG. 2 where the driving force is large at point A, small at point C and zero at point B. FIG. 2 also illustrates the concept that a dense solution of polymers or polymers dispersed in a network of gel fibers may be regarded as being confined to a hypothetical tube. The trailing end of the polymer must follow the path taken by the leading end. The model illustrated in FIG. 2 is supported and explained by Doi and Edwards, "The Theory of Polymer Dynamics", *International Series of Monographs on Physics,* Oxford University Press (1986); Evans and Edwards, "Computer Simulation of the Dynamics of Highly Entangled Polymers", *F. Chem. Soc. Faraday Trans.,* 2:1891–1912 (1981); Deutsch, "Dynamic Monte Carlo Simulation of an Entangled Many-Polymer System", *Am. Phys. Soc.,* 44:926–929 (1982); Skolnick, Kolinski and Yaris, "Monte Carlo Studies of the Long-Time Dynamics of Dense Polymer Systems-The Failure of the Reptation Model", *Acct. Chem. Res.* 20:350–356 (1987); Lerman and Frisch, "Why Does the Electrophoretic Mobility of DNA in Gels Vary With the Length of the Molecule?", *Biopolymers,* 21:995–997 (1982); Lumpkin and Zimm, "Mobility of DNA in Gel Electrophoresis", *Biopolymers,* 21:2315–2316 (1982); Lumpkin, DeJardin, and Zimm, "Theory of Gel Electrophoresis of DNA", *Biopolymers,* 24:1573–1593 (1985); Slater and Noolandi, "Prediction of Chain Elongation in the Reptation Theory of DNA Gel Electrophoresis", *Biopolymers,* 24:2181–2184 (1985); Slater and Noolandi, "On the Reptation Theory of Gel Electrophoresis", *Biopolymers,* 25:431–454 (1986); Viovy, "Molecular Mechanism of Field Inversion Electrophoresis", *Phys. Rev. Lett.,* 60:855–858 (1988); Noolandi, Rousseau and Slater, "Self-Trapping of Anomalous Dispersion of DNA in Electrophoresis", *Phys. Rev. Left.,* 58:2428–2431 (1987), Diwan and Schuster, "On the Theory of Gel Electrophoresis of DNA Extension and Evaluation of the Lumpkin-DeJardin-Zimm Model", *Analyt. Biochem.,* (1989); and Duke, "Tube Model of Field-inversion Electrophoresis", *Phys. Rev. Left.,* 62:2877–2880 (1989).

If the tube is not perfectly in alignment with the electric field, then the velocity in the direction of the electric field (z) will be less than the velocity along the tube defined by the polymer chain.

Figure 1:
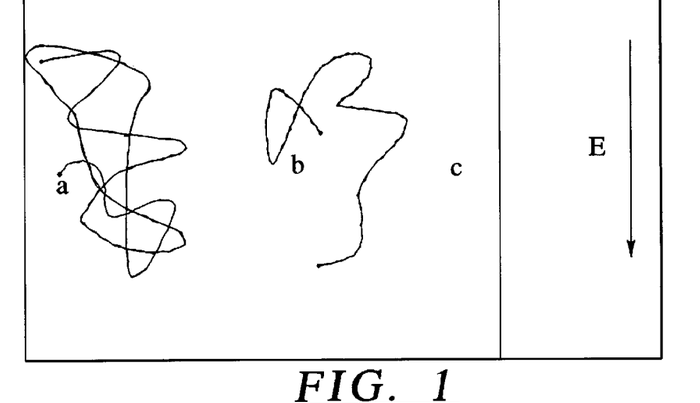
FIG. 1 illustrates typical configurations of charged polymer chains under the influence of an external field.

Further, DNA chains, when placed in a dense gel matrix and exposed to a weak, but constant electric field, are subject to thermal fluctuations. The thermal fluctuations tend to cause the chain of a moderate length to form random coils like that shown at (a) in FIG. 1. These coils exhibit properties of fractals because, when observed under a microscope, an increase in the magnification of the structure does not change the appearance of the chain. See Mandelbrot, *Fractal Geometry of Nature,* Freeman (1982) and Mandelbrot, *Fractals: Form, Change and Dimension,* Freeman (1977). The fractal characteristics of the DNA molecule is extremely important in terms of achieving size separation because the mobility equation for a chain in a gel is written as follows:

$$\mu_e = \mu_f < \left(\frac{h_z}{L}\right)^2 > \tag{1}$$

In order for the effective mobility $\mu_e$ to be dependent upon chain length L, the ratio $(h_z/L)^2$ must also depend upon chain length L. For a fractal, the term $(h_z)^2$ is proportional to $$<(h_z)^2> \alpha L^{2d_w} \tag{2}$$

where $d_w$ is a non-integer between 0 and 1 and is determined by the fundamental properties of the fractal object called fractal and spectral dimensions.

For a "random walk-like" structure, which may be created by thermal fluctuations $d_w=½$, which leads to $$<(h_z/L)^2> \alpha 1/L \tag{3}$$

and results in the desired dependence of the chain mobility on chain length $$\mu_e \alpha \mu_f L \tag{4}$$

As a result, separation by chain length is achieved.

However, for electric fields higher than 3 V/cm or even at lower strength fields where the DNA is greater than 50 kbp in length, the size-dependence of the electrophoretic mobility is lost because the DNA comes highly oriented in the field direction and no longer takes a tortuous, fractal path through the gel. See Fangman, "Separation of Very Large DNA Molecules by Gel Electrophoresis", Nucl. Acids Res., 5:653–665 (1978); Stellwagen, "Orientation of DNA Molecules and Agaros Gels by Pulsed Electric Fields", Biomolecular Structure and Dynamics, 3:299–314 (1985); Deutsch, "Explanation of Anamolous Mobility and Birefringence Measurements Found in Pulsed Field Electrophoresis", J. Chem. Phys., 90:7436–7441 (1989).

As a result, the value $d_w$ approaches 1 and $$<(h_z/L)^2> \alpha 1 \tag{5}$$

For DNA molecules greater than 50 kbp, the molecules tend to run together in the gel. Although the particles of a higher mass can be separated by reducing the electric field strength, there are drawbacks to this method. Most notably, an electrophoretic run using a reduced field strength can take a week or more to complete.

In an attempt to overcome the limitations of gel electrophoresis, pulsed field gel electrophoresis was developed. In this technique, an electric field is applied alternately in two or more different directions on an intermittent basis. This technique is described by Schwartz and Cantor, Cell, 37:67–75 (1984); U.S. Pat. No. 4,473,452; Smith and Cantor, Tibs, 12:284–287 (1987); Frank and Olsen, Science, 232:65–68 (1986) and U.S. Pat. No. 5,405,519.

Figure 3:
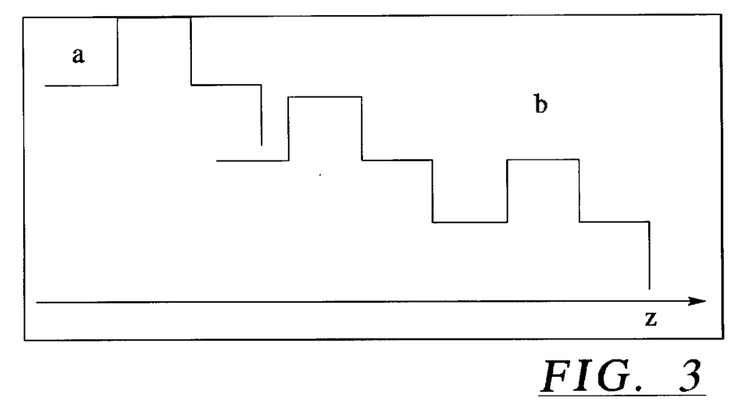
FIG. 3 illustrates example configurations achieved by a short chain and a longer chain under the influence of a deterministic pulse field.

However, the reorientation of the DNA under the pulsed electric fields does not lead to a fractal tube structure. Therefore, the separation by chain length is not achieved due to size-dependent mobility. The ratio of the projection of the tube on the z axis for the small chain a and for the larger chain b is the same as shown in FIG. 3.

Instead, separation by pulsed field gel electrophoresis is achieved due to a relaxation effect because the time required to reorient the DNA chain after a pulse is imposed depends upon the chain length. When the direction of the electric field is changed, small particles are reoriented quickly while larger particles remained substantially immobile until they are reoriented by the imposition of a new electric field. By the time the large particles begin to move in the new direction, the smaller particles will have substantially moved ahead of them thereby resulting in separation by size. The best results are obtained when the field strengths are relatively low and the pulse frequency is such that each molecule can change its confirmation at least once per pulse.

However, because the net forward migration of long chain molecules such as DNA molecules is slow, separation by pulsed field gel electrophoresis typically requires at least 24 hours. Sometimes, the separation requires as long as 200 hours.

Therefore, there is a need for an improved electrophoresis technique which overcomes the problems of traditional gel electrophoresis and pulsed field gel electrophoresis. Specifically, an improved electrophoresis technique is required which would enable the effective separation of longer chains such as larger DNA molecules and further which would achieve the separation in a time period that is less than currently provided by gel electrophoresis and pulsed field gel electrophoresis.

SUMMARY OF THE INVENTION

To address the aforenoted needs, the present invention provides a method and an apparatus for carrying out an improved electrophoresis technique. In accordance with the present invention, the method of separating larger particles from smaller particles includes the steps of applying a directional field across a medium in which the particles are suspended. The field includes a fractal field component and a steady field component. The fractal field arranges the particles into fractal space distributions in the medium while the steady field causes the particles to travel through the medium in a desired direction. The combination of the application of the fractal and steady fields results in smaller particles traveling through the medium along the desired direction at a faster rate than the larger particles.

In an embodiment, the steady field is an electric field that is applied across two electrodes that define the direction of travel through the medium.

In an embodiment, the steady field is an electric field that is imposed intermittently.

In an embodiment, the fractal field comprises a plurality of intermittent electric fields applied across the medium along the desired direction and at a plurality of angles with respect to the desired direction and in a random order.

In an embodiment, the fractal field is provided by a plurality of vibrators disposed around the medium at varying angles with respect to the desired direction, the vibrators being applied intermittently and in a random order with respect to each other and the steady field.

In an embodiment, the steady field is applied intermittently and the fractal field is provided by a plurality of acoustic transmitters disposed around the medium at varying angles with respect to the desired direction. The acoustic signals are transmitted by the acoustic transmitters on an intermittent basis.

In an embodiment, the fractal field is provided by a plurality of random and temporal space inhomogeneities of the medium.

In an embodiment, the medium in which the particles are dispersed comprises a matrix having fractal properties.

In an embodiment, the medium comprises a gel.

In an embodiment, the medium comprises a lithographic array.

In an embodiment, the particles are selected from the group consisting of polypeptide molecules, myosin acid molecules, hyaluronic acid molecules, nucleic acid-containing molecules and chromosomes.

The present invention also provides an apparatus for separating larger particles from smaller particles which includes a container for holding a medium in which the particles are suspended. The container has an inlet and an outlet and is disposed between two opposing primary electrodes. The two opposing primary electrodes are connected to a primary switching unit. The switching unit is connected to a controller. The two opposing primary electrodes generate an intermittent primary electric field across the medium in a forward direction from the inlet of the container towards the outlet of the container. The primary direction defines the direction in which the particles travel through the medium. The two opposing primary electrodes also generate an intermittent reverse primary electric field across the medium in a reverse direction from the outlet towards the inlet. The apparatus further comprises at least one pair of secondary opposing field generators disposed on opposing sides of the container at a secondary angle with respect to the inlet and the outlet. The secondary field generators are connected to a secondary switching unit. The secondary field generators generate an intermittent forward secondary field across the medium at the secondary angle with respect to the forward direction and an intermittent reverse secondary field across the medium at the secondary angle with respect to the reverse direction. The controller sends signals to the primary and secondary switching units to apply the primary forward electric field, primary reverse electric field, secondary forward field and secondary reverse field in a random order thereby creating a fractal field environment.

In an embodiment, the apparatus comprises two pairs of secondary opposing field generators.

In an embodiment, the secondary angle of the first pair of secondary field generators is about 120° with respect to the forward direction and the secondary angle of the second pair of field generators is about 60° with respect to the forward direction.

In an embodiment, the field generators are electrodes and, optionally, the primary and secondary switching units are consolidated into a single switching unit.

In an embodiment, the field generators are vibrators.

In an embodiment, the field generators are acoustic transmitters.

It is therefore an advantage of the present invention to provide an improved electrophoretic method of separating particles by size.

Another advantage of the present invention is to provide an improved method of separating large DNA molecules.

Another advantage of the present invention is to provide an apparatus for carrying out an improved electrophoresis technique.

Yet another advantage of the present invention is to provide improved electrophoretic methods that are faster and provide greater resolution than currently available electrophoretic techniques.

Other objects and advantages of the present invention will become apparent upon reading the detailed description of the invention, the accompanying drawings and appended claims.

BRIEF DESCRIPTION OF THE DRAWING

The present invention is described more or less diagrammatically in the following drawings wherein.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

The present invention provides an improved method and apparatus for carrying out separations by electrophoresis by applying a fractal field across the medium in which the particles to be separated are suspended. The fractal field applied to the medium arranges the molecules or particles to be separated in entangled coils having fractal properties. The application of a steady field component to the medium drags the molecules through the field. By insuring that the molecules and/or field have fractal properties, separation is assured even for larger molecules of greater than 50 kpb and even when a steady component electric field is applied that is greater than 3 V/cm. Thus, separation is provided for larger molecules and when a strong steady field component is applied thereby assuring faster separation times. In one embodiment illustrated in FIG. 5, the particles undergoing separation are subject to an external fractal field. In a second embodiment illustrated in FIGS. 4 and 6, the solvent or separation matrix is manipulated so that it has fractal properties.

Figure 4:
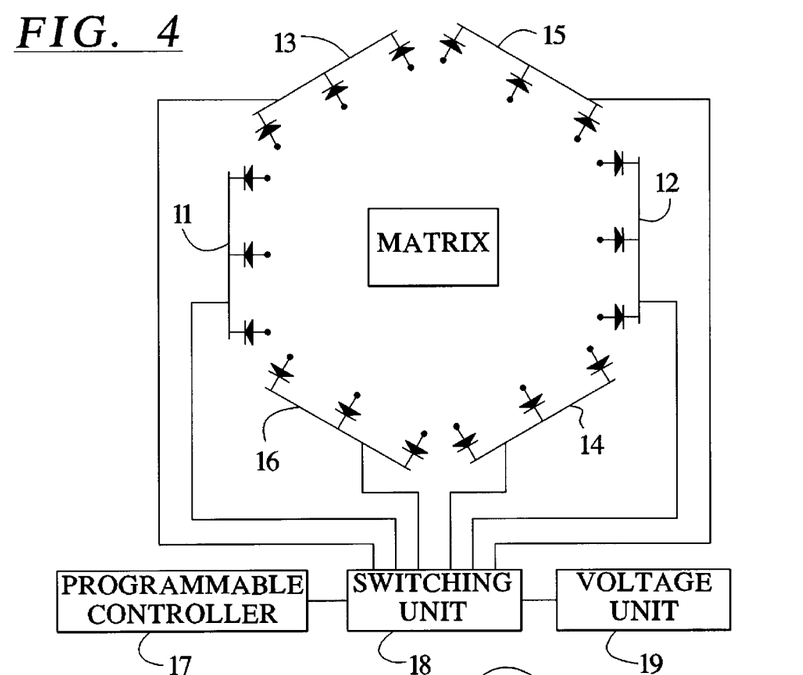
FIG. 4 is a schematic illustration of an apparatus for carrying out the electrophoretic separation method of the present invention.
Figure 5:
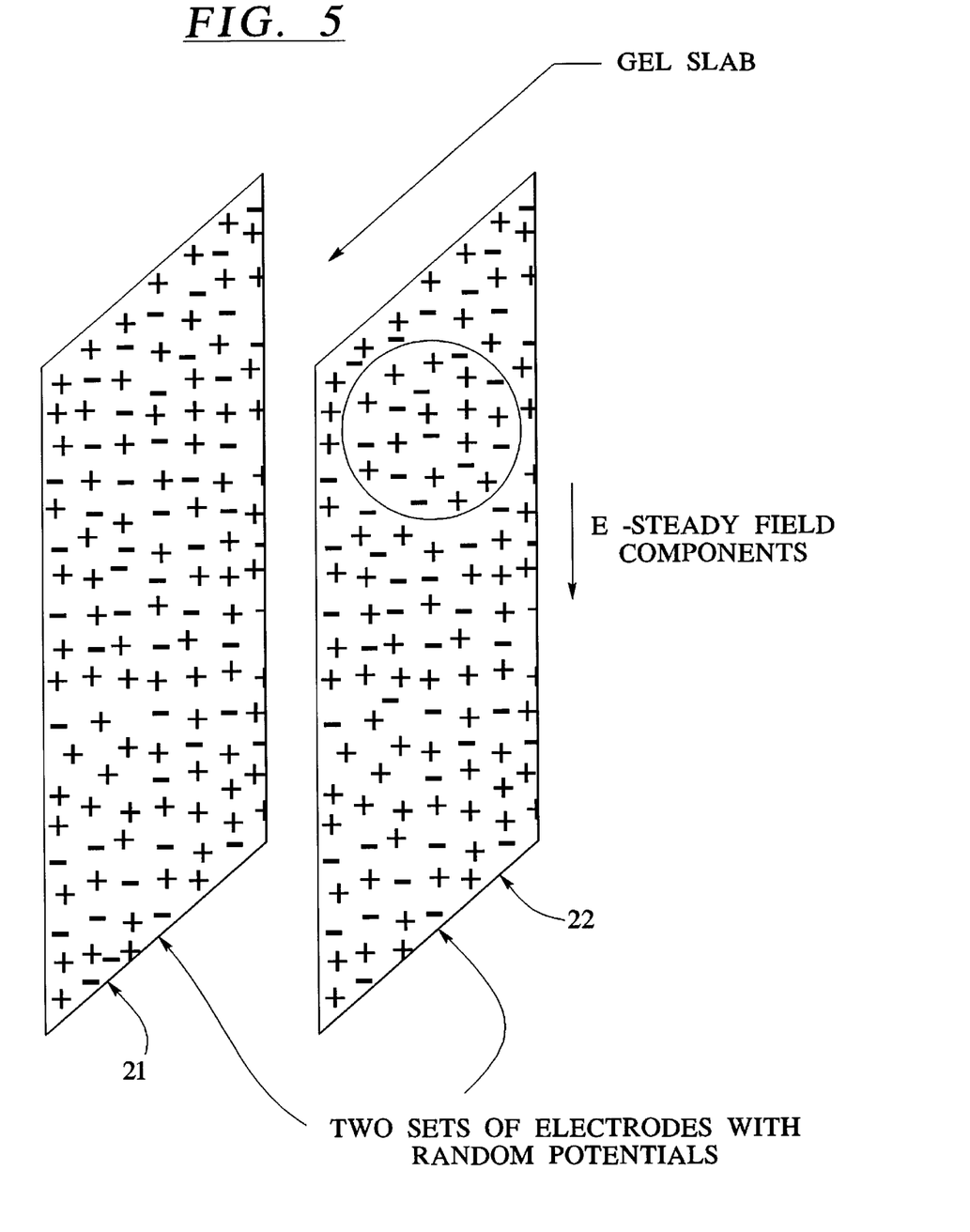
FIG. 5 is a schematic illustration of one pair of opposing electrodes that can be used in an alternative embodiment to the apparatus shown in FIG. 4.
Figure 6:
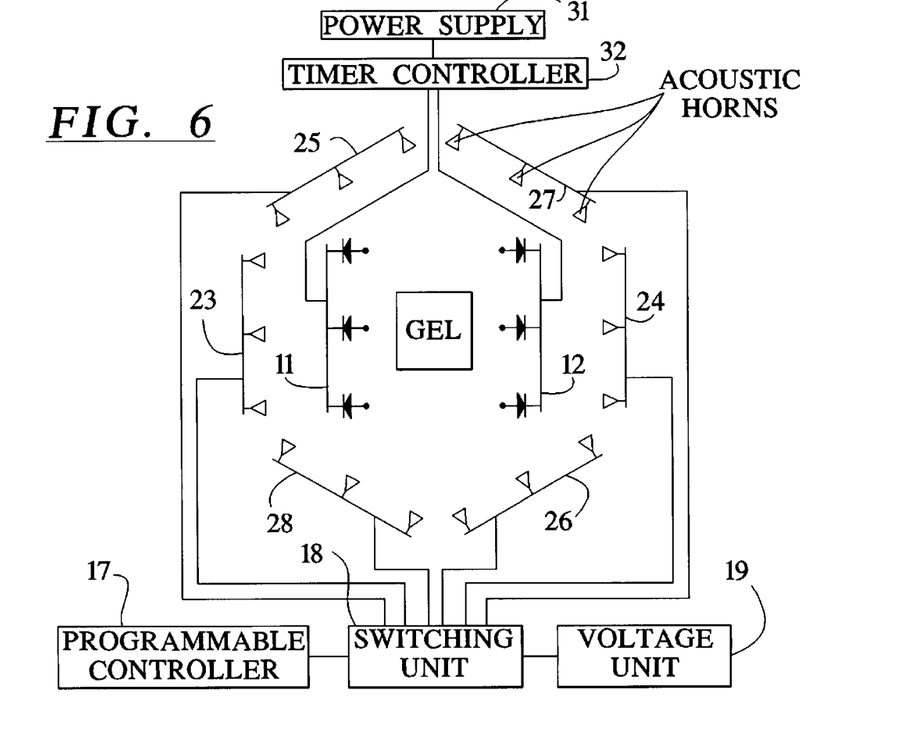
FIG. 6 is a schematic illustration of another apparatus for carrying out the electrophoretic separation method of the present invention.

There are different ways to create a deterministic or random field sequence with fractal properties. One method is illustrated in FIGS. 4 and 6 and another method is illustrated in FIG. 5 which will be discussed below. The important point is that for any fractal sequence, the averaged vector sum of any N subsequent field intensities be proportional to $N^{d_f}$ with non-integer power $d_f$ being greater than zero and less than 1. An example which is discussed below is a random field sequence of pulses wich constant amplitude and duration, and with random directions. In one particular type of such a random sequence, the directions of the field in two subsequential pulses is equal to $\pm\Theta$, where $\Theta$ is a constant angle and the choice of plus or minus sign is random for each pulse. The correlations between subsequent pulses rapidly decrease with time, in the simplest case, all angles between subsequent pulses should be random and mutually independent. Each pulse will pull a part of the chain from the former tube, elongate it in the current pulse direction, eliminate one tube step, and form a new step of the tube, see FIG. 7. The amplitude of each pulse should be large enough to overcome the thermal fluctuations and large compared to the steady field component in order to keep the random walk-type structure of the tube.

The desired random structure of the tube, which is crucial for the separation, is not dependent on thermal fluctuations and on the gel structure. The length and the orientation of a step of the tube is controlled by the amplitude, duration time, and direction of a random pulse. However, the tube step should be larger than the mean distance between the obstacles in the separation matrix, a. The number of steps of the tube is determined by the chain length and the length of the tube step in contrast to conventional gel electrophoresis (GE) and pulsed field gel electrophoresis (PFG).

In conventional GE, the tube step is roughly equal to a and the random structure of the tube is caused and controlled by thermal fluctuations. This results in severe limitations on the maximum length of the molecules that can be separated and imposes a necessity to reduce the field, which leads to an increase of the separation time. As discussed above, the periodic structure of tubes crated by the regular pulsed field in conventional PFG does not provide the desired dependence of the mobility on chain length and the separation is achieved by the second order effects related to the difference in reorientation times for chains of different lengths.

In contrast, the random structure of the tubes created by the random field in the frame of the present invention will provide such a dependence. Choosing an obtuse angle Θ, say Θ=120°, sharp angles between subsequent tube steps are avoided which minimized the unwanted DNA trapping and which also dramatically increases the separation time in conventional GE and in PFG. The trapped chains will be effectively released by application of random pulses. The fact that the tube structure virtually does not depend on a, permits the decrease of the gel concentration and the use of other separation matrixes like micro lithographic arrays, which in turn, will decrease the unwanted overall friction of the media.

The second embodiment of the invention fractal field is constant in time but random in space. The random field might be created by the set of microelectrodes with random potential placed on both sides of the separation matrix, see FIG. 5, or by random hydrodynamic fields, see FIG. 6.

Referring now to FIG. 4, a block diagram of the one embodiment of the apparatus of the present invention is shown which can be used for FFE method in random field time-sequences embodiment. The application of steady component of the field will be implemented through voltage applied to two sets of electrodes, 11, 12. The application of the random component will be implemented through computer-controlled switching of voltages applied to six arrays of three electrodes each, shown at 11-12, 13-14 and 15-16. Desired fields, reorientation angles, and pulse times will be generated by a computer which is in communication with a switching unit 18. Voltage for generating the fields is provided by the voltage unit 19.

The possible elements of the sequences of the directions of pulses of the random field is prescribed by the following transition matrix. This matrix determines the possible sequential pairs of the orientations of the random field exposed by the external electrodes sets presented in FIG. 4. Of course, other variations are possible.

| Direction of the Current Field | 14→13 | 12→11 | 15→16 | 13→14 | 11→12 | 16→15 |
|---|---|---|---|---|---|---|
| Direction of the Possible Successor | 16→15<br>12→11 | 14→13<br>15→16 | 13→14<br>12→11 | 15→16<br>11→12 | 11→17<br>16→15 | 14→13<br>11→12 |

For each pulse, the computer will pick up one of two random numbers, say 0 and 1. The first number, 0, will correspond to the choice from the second row of the transition matrix, 1 will correspond to the third row of the transition matrix. Thus, the field direction for each new step will be determined by the current field direction, the random number picked up by the computer, and the transition matrix. This will provide a random tube with the fractal "random-walk type" scaling relation, and with the angle ±120° between any two successive steps.

FIG. 5 illustrates two sets of micro-electrodes 22 for generating an electric field with fractal spacial properties. Thus, as opposed to applying fields of different directions in random sequence as set forth above with respect to FIG. 4, one pair of sets of electrodes 21, 22 may be applied to generate a field with fractal spacial properties.

Turning to FIG. 6, instead of the three diametrically opposed pairs of electrodes 11-12, 13-14 and 15-16 shown in FIG. 4, one pair of diametrically opposed electrodes 11-12 is provided for generating a steady field and three diametrically opposed sets of acoustic horns shown at 23-24, 25-26 and 27-28 are provided which, when applied in a random sequence similar to that set forth above for FIG. 4, generate fractal properties in the separation matrix or medium. In the embodiment illustrated in FIG. 6, a separate power supply 31 and time controller 32 are provided for controlling the electrodes 11-12. Because the electrodes 11-12 do not need to be used to create the fractal spacial properties, the field applied by the electrodes 11-12 need only be applied in a single direction, from the electrode set 11 to the electrode set 12. Accordingly, the electrode sets 11, 12 need not be linked to a switching unit or mechanism.

Figure 7:
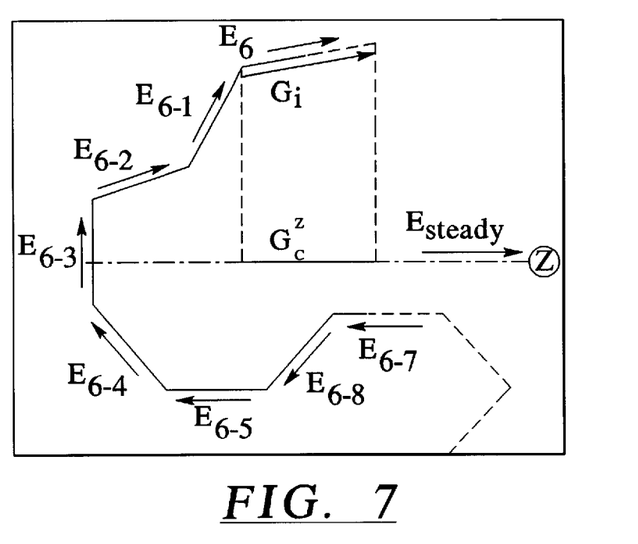
FIG. 7 is an illustration of a typical tube configuration created by a random field.

A typical tube configuration created by the random field is illustrated in FIG. 7. The solid line shows the eight tube segments which are occupied by the chain during the pulse number i, dashed line shows the two segments of the "former" tube which were occupied during the pulses number i-1 and i-2. The segments number $\underline{i}$ and number i-7 are shown in part by dashed lines and in part by solid lines since the former is being created by the motion of the leading end of the chain while the latter is being released by the trailing end of the chain during the pulse number i. The vector $E_j$, j=i, i-1, i-7, indicate the field direction and amplitude for the pulse number j. The vector $G_i$ indicates the displacement of the leading end of the chain caused by the pulse number i. The length of the tube step number i is $|G_i|$ and $G_i^z$ is the projection of the tube segment on the direction of the steady field component.

The results for the dynamics of a charged polymer chain, with the total charge Z, moving in a random media subject to random external field pulses $E_i$, i=1, 2 ... M, along with a steady regular component, $E_{steady}$ are as follows. The random pulses have a constant amplitude $|E_i|_{=ER}$ and duration τ, and random directions. The overall number of pulses M=t/τ, where t is the total separation time. In the presented below derivation, we follow the general methods and approximations adopted in biased reptation model and consider the case when $E_R \gg E_{steady}$.

During the pulse number i, when the time is $i\tau \leq t < (i+1)\tau$, the field $E_i + E_{steady}$ drags the chain along the tube which has been created by the pulses with numbers i-1, i-2, ... i-K, destroys one tube step at the trailing end, and forms a new tube step at the leading end (see FIG. 7). Here K is the number of the steps of the tube for the chain of the given length. For the stretched chain[2], the total tube length is equal to the chain length L, and $$KG = L, \qquad (6)$$

where G is the average length of the tube step.

The new tube step is determined by the displacement of the leading end of the chain during the pulse, $G_i$. For strong random field/large chain, i.e. when $$\frac{Q|\vec{G}_i|E_R}{Lk_B T} \gg 1, \qquad (7)$$

$$\vec{G}_i = \mu_f \tau (\vec{E}_i + \vec{E}_{steady}) \frac{\left| \sum_{j=1}^{K} G_{i-j}^{E_i + E_{steady}} \right|}{L}, \qquad (8)$$

where $$G_{i-j}^{E_i + E_{steady}} \qquad (9)$$

is the projection of the tube segment created by the pulse number i-j on the direction of the overall field, $E_i + E_{steady}$, produced by the pulse number i and by the steady field component. The product $\mu_f \tau(E_i + E_{steady})$ is equal to the displacement which a free chain subject to the driving force $E_i + E_{steady}$ would have in a liquid solution with the same effective friction as in the separation matrix during the pulse time $\tau$. It can be presented in terms of the steady velocity, $\dot{z}$, of chain completely elongated along the steady field with the amplitude equal to $(E_i + E_{steady}) - \mu_f \tau(E_i + E_{steady}) = \dot{z}\tau$. The term $$\sum_{j=1}^{K} G_{i-j}^{E_i + E_{steady}}$$

is equal to the overall projection of the chain in the given configuration on the direction of the $E_i + E_{steady}$. Thus, the driving force along the tube is reduced with respect to the free drag in a liquid solution in proportion to the ratio $$\frac{\left| \sum_{j=1}^{K} G_{i-j}^{E_i + E_{steady}} \right|}{L} \qquad (10)$$

For each pulse, the choice of the leading or trailing chain ends depend on the orientation of the tube with respect to the current field direction, i.e. the direction of the field and the induced motion of the chain along the tube coincides with the direction of the net force moving the chain along the tube. Therefore, we use the absolute value of $$\sum_{j=1}^{K} G_{i-j}^{E_i + E_{steady}}$$

in the Equation (8) above.

Adopting the self consistent field (mean field) type approximation we estimate the average length of a tube step.

$$G = \mu_f \tau (E_R + E_{steady}) \frac{\left\langle \left| \sum_{j=1}^{K} G_{i-j}^{E_i + E_{steady}} \right| \right\rangle}{L}, \qquad (11)$$

where $E_R$ is an amplitude of the random field and $\langle \rangle$ stands for the time averaging. The term $$\left\langle \left| \sum_{j=1}^{K} G_{i-j}^{E_i + E_{steady}} \right| \right\rangle \qquad (12)$$

is the average absolute value of the sum of K random variables $$G_{i-j}^{E_i + E_{steady}}.$$

Each of these variables is determined by the Equation (8) and has a random component provided by the random field, and a steady component, caused by the steady field component. The random component of a tube step is proportional to $$\frac{E_R}{E_R + E_{steady}}, \qquad (13)$$

the regular component of a tube step is proportional to $$\frac{E_{steady}}{E_R + E_{steady}} \qquad (14)$$

Following the mean field approximation, we assume that $$G_{i-j}^{E_i + E_{steady}} \approx G$$

and that the random components of different tube steps are mutually independent. Thus, for $K \gg 1$ $$\left\langle \left| \sum_{j=1}^{K} G_{i-j}^{E_i + E_{steady}} \right| \right\rangle \approx \frac{G}{E_R + E_{steady}} (E_R \sqrt{K} + K E_{steady}) \qquad (15)$$

Substituting the Equation (15) into the Equation (11) in the limit $E_{steady} \ll 1$, we obtain $$\frac{L}{\sqrt{K}} = \mu_f \tau E_R \left( 1 + \sqrt{K} \frac{E_{steady}}{E_R} \right) \qquad (16)$$

Finally, in the most interesting and important limiting case when $$\sqrt{K} \frac{E_{steady}}{E_R} \ll 1 \qquad (17)$$

$$K = \left( \frac{L}{\mu_f E_R \tau} \right)^2 \qquad (18)$$

In qualitative terms, the Equation (18) shows that the average number of tube steps is proportional to the length of the chain and inversely proportional to the average length of a tube step, while the tube step length increases with the strength of the random field and decreases due to the constraints caused by the tube.

The overall displacement of the DNA along the steady component of the field equals to $$\vec{S}_Z = \tau \mu_f \vec{E}_{steady} \sum_{i=1}^{M} \left( \frac{\sum_{j=1}^{K} G_{i-j}^z}{L} \right)^2, \qquad (19)$$

where $G^z_m$ is the length of the projection of the tube segment created by the field pulse number m on the direction of the steady field component and the term $$\tau \mu_f \vec{E}_{steady} \left( \frac{\sum\limits_{j=1}^{K} G_{i-j}^z}{L} \right)^2 \quad (20)$$

is the displacement of the chain along $E_{steady}$ during the pulse number i (compare to the Equation (1)). Here the product $\tau \mu_f E_{steady}$ is equal to the displacement which a free chain subject to the driving force $E_{steady}$ would have in a liquid solution during the pulse time $\tau$ and the term $$\sum\limits_{j=1}^{K} G_{i-j}^z \quad (21)$$

is equal to the overall projection of the chain in the configuration corresponding to the pulse number i on the direction of the steady field component. Both the driving force along the tube with respect to the driving force on a free chain in a liquid solution and the velocity of the chain along the steady field component with respect to the velocity along the tube, are reduced in proportion to the same ratio, namely $$\frac{\left| \sum\limits_{j=1}^{K} G_{i-j}^{E_i + E_{steady}} \right|}{L} \quad (22)$$

Thus, the velocity of the chain along the steady field component is reduced with respect to the velocity in a free liquid solution by $$\left( \frac{\sum\limits_{j=1}^{K} G_{i-j}^z}{L} \right)^2 \quad (23)$$

Substituting $$G_{i-j}^z \approx G \left( \frac{E_{i-j}^z}{E_R} + \frac{E_{steady}}{E_R} \right) \quad (24)$$

and taking advantage of the Equation (6) we obtain $$\vec{S}_Z = \mu_f \frac{\vec{E}_{steady} t}{K} \left( 1 + K \frac{E_{steady}}{E_R} + \Delta \right), \quad (25)$$

where $$\Delta = \frac{1}{MK} \left( 2KE_{steady} \sum\limits_{i=1}^{M} \frac{E_{i-j}^z}{E_R} + 2 \sum\limits_{i=1}^{M} \sum\limits_{j=1}^{K} \sum\limits_{k=1}^{j-1} \frac{E_{i-j}^z E_{i-j}^z}{E_R^2} \right) \quad (26)$$

Since the values of $E_{i-j}^z/E_R$ are identically distributed random variables with zero mean value and M is a large number $$\Delta \propto \frac{\sigma}{\sqrt{M}} \left( 2 \frac{E_{steady}}{E_R} + K\sigma \right), \quad (27)$$

where $\sigma$ is the dispersion of the normalized random field, $$\sigma = \sqrt{\left\langle \left( \frac{E_{i-j}^z}{E_R} \right)^2 \right\rangle} \quad (28)$$

Finally, for M>>1 taking advantage of the Equation (18) and of the definition of electrophoretic mobility, we obtain $$\mu_e = \mu_f \left( \frac{\mu_f E_R \tau}{L} \right)^2 \left( 1 + \left( \frac{L}{\mu_f E_R \tau} \right)^2 \frac{E_{steady}}{E_R} + \ldots \right) \quad (29)$$

Choosing the experimental parameters $\tau$ and $E_R$ such that $\tau \mu_f E_R = L_{min}/2$, where $L_{min}$ is the expected minimum chain length which is to be separated, and turning to the normalized mobility, $\mu = \mu_e/\mu_f$, and the normalized chain length, $x = L/L_{min}$, we obtain a universal dependence $$\mu = \left( \frac{1}{2x} \right)^2 \left( 1 + \frac{E_{steady}}{E_R} (2x)^2 \right) \quad (30)$$

Figure 8:
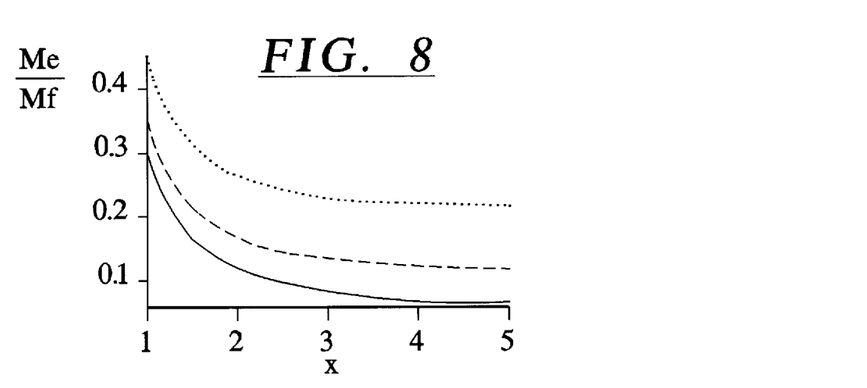
FIG. 8 illustrates, graphically, the dependence of normalized mobility on normalized chain length for the method and apparatus of the present invention.
Figure 9:
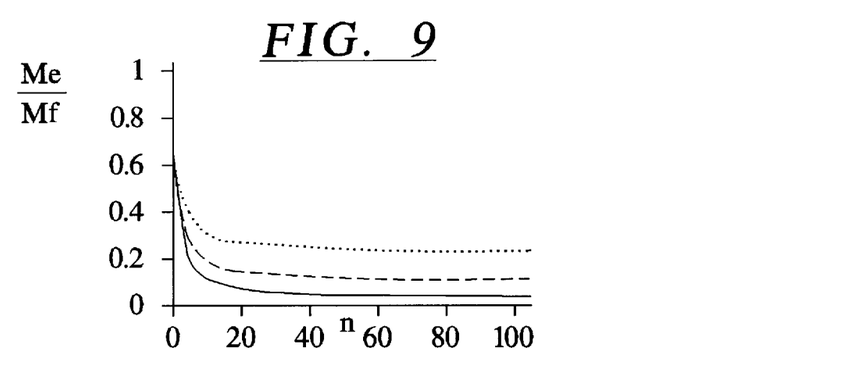
FIG. 9 illustrates, graphically, the normalized mobility versus chain length for a conventional gel electrophoresis separation method.
Figure 12:
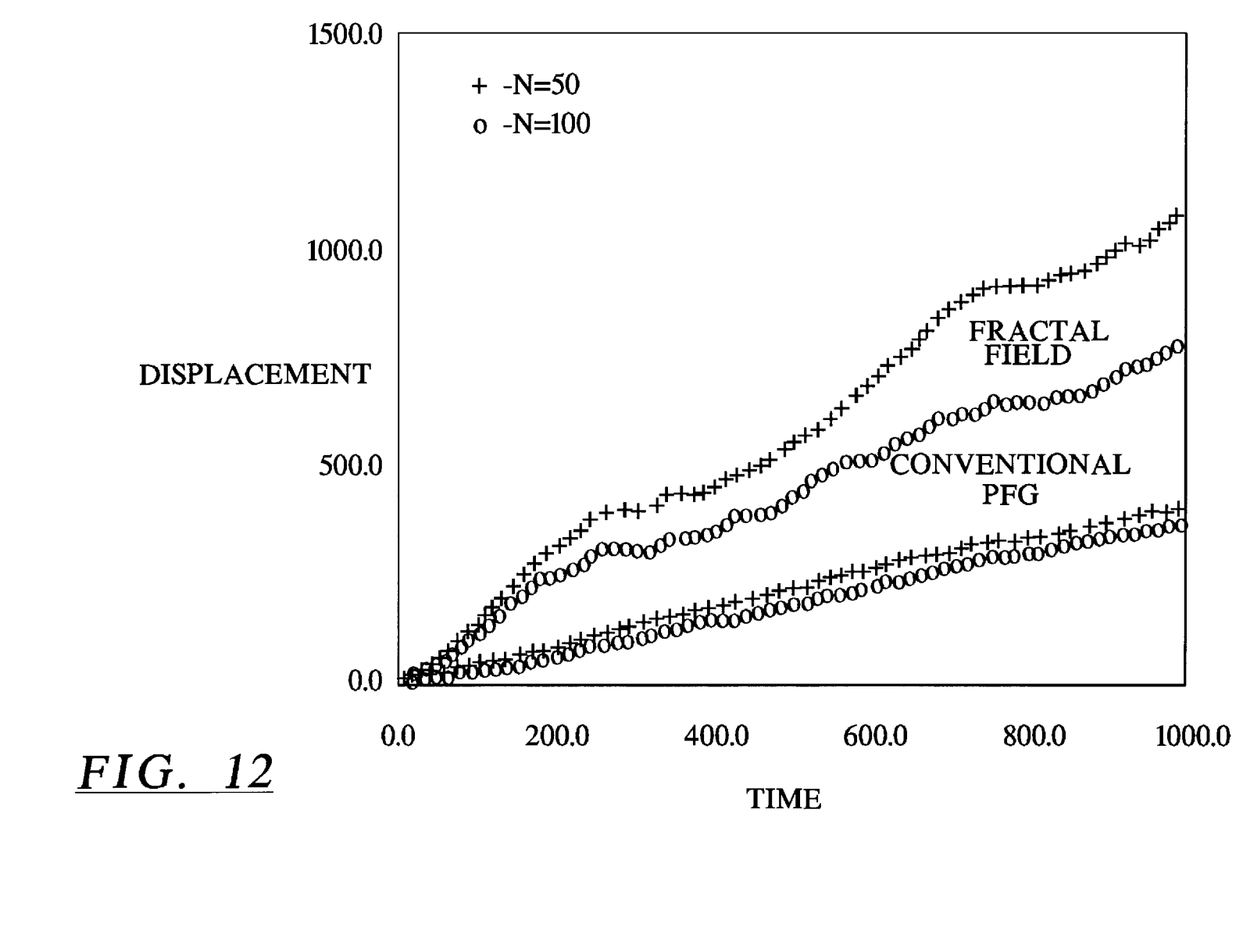
FIG. 12 illustrates, graphically, a comparison of the displacement of DNA of varying chain lengths in a random field in accordance with the present invention and conventional techniques.

The dependence of normalized mobility on the normalized chain length with the experimental parameters adopted from Schwartz and Cantor, "Separation of yeast Chromosome-Sized DNA by Pulsed Field Gradient Gel Electrophoresis", Cell, 37:67 (1984) is presented in FIG. 9. Thus, in the following range of parameters $$\left( \frac{L}{\tau \mu_f E_R} \right) >> 1, t/\tau >> 1, \text{ and } \left( \frac{L}{\tau \mu_f E_R} \right)^2 \frac{E_{steady}}{E_R} << 1, \quad (31)$$

the method of the present invention provides a sharp separation caused by the inverse proportionality of the mobility to squared chain length as predicted by Equation (29) and illustrated in FIGS. 8 and 12. It is important that contrary to the constant field GE where the cut off length is determined by the thermal fluctuations, in the FFE of the present invention, the range of separation lengths is controlled by the experimental parameter $\tau \mu_f E_R$ which can be varied.

In numerical simulations, the polymer molecule is represented by a chain of N beads, each carrying a charge of one. The beads are connected by unstretchable but freely hinged bonds of length l. The gel is modeled by a two-dimensional square lattice of obstacles of a period one. There is a short-range repulsive force between obstacles and the beads of the chain. The force is chosen to completely prohibit the chain crossing an obstacle; we use the following expression for the force:

$$f(r) = A \left( \frac{1}{r^2} - \frac{1}{r_c^2} \right)^2 \quad (32)$$

Here r is a distance between a bead and a force center, $r_c$ and A are the range and the amplitude of the force, correspondingly. The effects of the temperature are represented by a Gaussian random force of the amplitude $T^{1/2}$ that acts on each beat independently. The motion of the chain through the lattice under the action of electric field E and random forces is considered to be overdamped, i.e. the velocity of a bead is proportional to the sum of all force acting on it. Numerical simulations of the model for the following parameters were performed: N=10, 20, 50, 100, I=0.25, rc=0.4, A=1, E=$3^{1/2}$. The thermal forces are randomly updated for each time step with their square average being proportional to the temperature T. The temperature is maintained at about 5° C. The angle between the electric field E and the axis of the lattice of obstacles is chosen to be 54° to prevent scattering-free propagation. In the second part of simulation, a "random" electric field is added with an amplitude $E_r$=5. The direction of this field is changed with a period of $\tau$=2 by being randomly increased or decreased by 120°.

Figure 10:
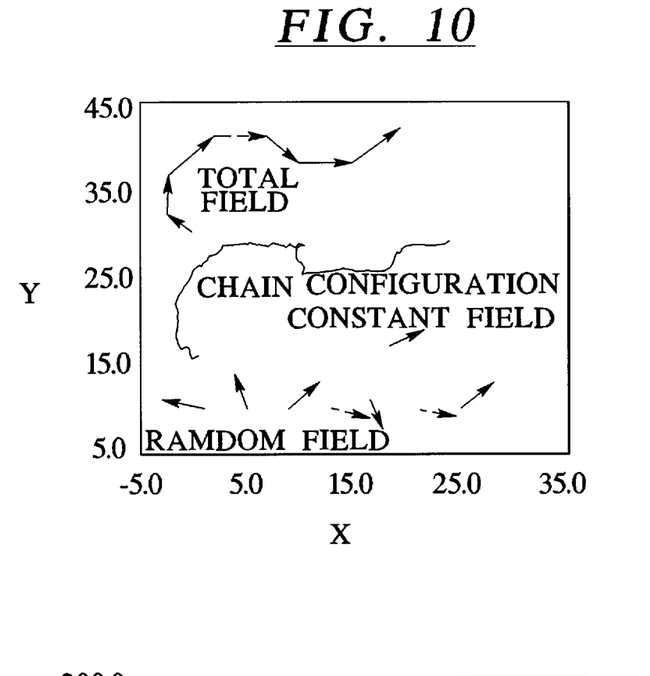
FIG. 10 illustrates, graphically, subsequent positions of a chain with 50 segments dragged through obstacles under the influence of a random field with a steady component in accordance with the present invention.
Figure 11:
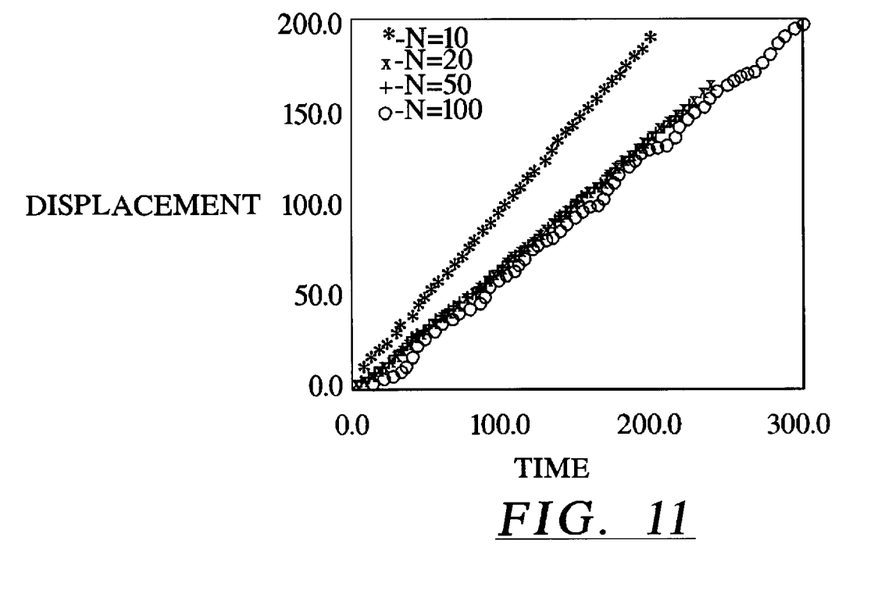
FIG. 11 illustrates, graphically, the displacement of DNA of varying chain length in a constant field.

The results of numerical experiments are presented in FIGS. 10, 11 and 12. The results presented in FIG. 10 show the typical subsequent configurations of the N=50 chain in an external random field. The orientation of the chain is determined by the overall field (compare to the FIG. 7). In a constant field (FIG. 11), N=10 chains run faster than larger ones while N=20, 50, and 100 chains cannot be separated. In a fractal field (FIG. 12), with random independent choice of ±120° angle between two successive orientations of the random field component, $E_R/E_{steady}$=2.8868 and τ=2 (measured in "Molecular Dynamics steps") a significant separation of N=100 and 50 chains and overall increase of mobility compared to the constant field is observed. In accordance with the present invention, the two chains move coherently and accelerate and slow down at the same time, but the longer chain gets smaller acceleration and slows down more than the shorter chains.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. A method of separating larger particles from smaller particles which are suspended in a medium, the method comprising:
    applying a field across the medium, the field comprising a fractal component and a steady component, the fractal component arranging the particles into fractal space distributions in the medium, the steady component causing the particles to travel through the medium in a desired direction, the combination of the application of the fractal and steady components resulting in the smaller particles traveling through the medium along the desired direction at a faster rate than the larger particles.

2. The method of claim 1 wherein the steady component is an electric field applied across two electrodes.

3. The method of claim 1 wherein the steady component is an intermittent electric field applied across two electrodes.

4. The method of claim 1 wherein the fractal component comprises a plurality of intermittent electric fields applied across the medium along the desired direction and at a plurality of angles with respect to the desired direction and in a random order.

5. The method of claim 1 wherein the steady component is applied intermittently and wherein the fractal component is provided by a plurality of vibrators disposed around the medium at varying angles with respect to the desired direction.

6. The method of claim I wherein the steady component is applied intermittently and wherein the fractal component is provided by a plurality of acoustic transmitters disposed around the medium at varying angles with respect to the desired direction.

7. The method of claim 1 wherein the fractal component is provided by a plurality of space inhomogeneities of the medium.

8. The method of claim 7 wherein the plurality of space inhomogeneities of the medium is provided by a plurality of acoustic transmitters disposed around the medium at varying angles with respect to the desired direction.

9. The method of claim 7 wherein the plurality of space inhomogeneities of the medium is provided by a plurality of vibrators disposed around the medium at varying angles with respect to the desired direction and applied intermittently and in a random order with respect to each other and the steady field.

10. The method of claim 7 wherein the medium is a solvent contained within a separation matrix and the plurality of space inhomogeneities of the medium is provided by generating turbulent flow of the solvent in the separation matrix.

11. The method of claim 7 wherein the medium is free liquid solution and the plurality of space inhomogeneities of the medium is provided by generating turbulent flow of the free liquid solution.

12. The method of claim 1 wherein the medium comprises a matrix having fractal properties.

13. The method of claim 1 wherein the medium comprises a gel.

14. The method of claim 1 wherein the medium comprises a lithographic array.

15. The method of claim 1 wherein the particles are selected from the group consisting of polypeptide molecules, myosin acid molecules, hyaluronic acid molecules, nucleic acid-containing molecules and chromosomes.

16. A method of separating larger particles from smaller particles, the method comprising the following steps:
    suspending the particles to be separated in a medium,
    applying a plurality of intermittent electric fields across the medium including a steady field in a forward direction and a plurality of other fields that are aligned at varying angles with respect to the the forward direction, only one of the steady field or one of the other fields being applied at a time, the steady and other fields being applied in a random order, the steady field causing the particles to travel through the medium in the forward direction, the other fields creating fractal space distributions amongst the particles suspended in the medium, whereby the combination of the application of the steady and the other fields resulting in the smaller particles traveling through the medium in the forward direction at a faster rate than the larger particles.

17. The method of claim 16 wherein the directional pulses are sound wave pulses generated by a plurality of vibrators disposed around the medium at varying angles with respect to the forward direction.

18. A method of separating larger particles from smaller particles, the method comprising the following steps:
    suspending the particles to be separated in a medium,
    applying an electric field across the medium, and
    applying a plurality of directional pulses to the medium at varying random angles with respect to a forward direction defined by the electric field, the electric field causing the particles to travel through the medium in the forward direction, the directional pulses creating fractal space distributions amongst the particles suspended in the medium, whereby the combination of the application of the electric field and the directional pulses resulting in the smaller particles traveling through the medium in the forward direction at a faster rate than the larger particles.

19. The method of claim 18 wherein the directional pulses are sound wave pulses generated by a plurality of acoustical transmitters disposed around the medium at varying angles with respect to the forward direction.

20. An apparatus for separating particles suspended in a medium by particle size, the apparatus comprising:
    the medium being disposed between two opposing primary electrodes,
    the two opposing primary electrodes being connected to a primary switching unit, the switching unit being connected to a controller, the two opposing primary electrodes for generating an intermittent primary electric field across the medium in a forward direction, the two opposing primary electrodes also for generating an intermittent reverse primary electric field across the medium in a reverse direction, at least one pair of secondary opposing field generators disposed at a secondary angle with respect to the forward direction, the secondary field generators being connected to a secondary switching unit, the secondary field generators for generating an intermittent forward secondary field across the medium at the secondary angle with respect to the forward direction, the secondary field generators also for generating an intermittent reverse secondary field across the medium at the secondary angle with respect to the reverse direction, the secondary field generators being selected from the group consisting of vibrators and acoustic transmitters, the controller sending signals to the primary and secondary switching units to apply the primary forward electric field, primary reverse electric field, secondary forward field and secondary reverse field in a random order.

21. The apparatus of claim 20 wherein the apparatus comprises two pairs of secondary opposing field generators.

22. The apparatus of claim 21 wherein the secondary angle of the first pair of secondary field generators is about 120° with respect to the forward direction, the secondary angle of the second pair of field generators is about 60° with respect to the forward direction.

23. The apparatus of claim 20 wherein the primary and secondary switching units are provided by a single switching unit.

24. An apparatus for separating particles suspended in a medium by particle size, the apparatus comprising:

the medium being disposed between two opposing primary electrodes, the two opposing primary electrodes being connected to a switching unit, the switching unit being connected to a voltage unit and a controller, the two opposing primary electrodes for generating an intermittent primary electric field across the medium in a forward direction, the two opposing primary electrodes also for generating an intermittent reverse primary electric field across the medium in a reverse direction, at least one pair of secondary opposing electrodes disposed at a secondary angle with respect to the forward direction, the secondary electrodes being connected to the switching unit, the secondary electrodes for generating an intermittent forward secondary electric field across the medium at the secondary angle with respect to the forward direction, the secondary electrodes for generating an intermittent reverse secondary electric field across the medium at the secondary angle with respect to the reverse direction, the controller sending signals to the switching unit to apply the primary forward field to generate a steady field component, the controller further sending signals to the switching unit to apply the primary forward, primary reverse, secondary forward and secondary reverse electric fields in a random order to generate a fractal field component.

25. The apparatus of claim 24 wherein the apparatus comprises two pairs of secondary opposing electrodes.

26. The apparatus of claim 25 wherein the secondary angle of the first pair of secondary electrodes being about 120° with respect to the forward direction, the secondary angle of the second pair of electrodes being about 60° with respect to the forward direction.

\* \* \* \* \*